United States Patent [19]

Randall

[11] 4,451,278
[45] May 29, 1984

[54] 1-HYDROXYANTHRAQUINONE AQUATIC HERBICIDE

[75] Inventor: David I. Randall, Easton, Pa.

[73] Assignee: GAF Corporation, New York, N.Y.

[21] Appl. No.: 276,151

[22] Filed: Jul. 28, 1972

Related U.S. Application Data

[62] Division of Ser. No. 121,520, Mar. 5, 1971, abandoned.

[51] Int. Cl.$^3$ .............................................. A01N 35/04
[52] U.S. Cl. ............................................ 71/66; 71/94; 71/103; 71/106; 71/107; 71/118; 71/122; 71/123
[58] Field of Search ..................... 71/66, 67, 106, 122, 71/107, 94, 118, 103

[56] References Cited

U.S. PATENT DOCUMENTS 3,299,098  1/1967  Reifschneider .................... 71/66

OTHER PUBLICATIONS

Otto, Chem. Abst., vol. 47 (1953), 5495e.
Brain, Chem. Abst., vol. 40 (1946), 624.

Primary Examiner—Catherine L. Mills
Attorney, Agent, or Firm—Marilyn J. Maue; J. Gary Mohr; Joshua J. Ward

[57] ABSTRACT

A method of inhibiting the growth of weeds is provided by applying to the situs to be treated, an effective herbicidal amount of a compound containing the 1-anthraquinonyloxy moiety, such as 1-hydroxyanthraquinone.

9 Claims, No Drawings

1-HYDROXYANTHRAQUINONE AQUATIC HERBICIDE

This is a division of application Ser. No. 121,520, filed Mar. 5, 1971, now abandoned.

This invention relates to herbicidal compositions and processes therefor. More particularly, it relates to compositions and processes for selectively eradicating noxious weeds from aqueous and/or terrestrial bodies while simultaneously demonstrating substantially no harmful effects toward aquatic life or crops.

The use of aqueous bodies such as lakes, rivers, ponds, streams, marshes, swamps and the like for purposes of recreation as well as life support for the aquatic life therein is continually threatened by the encroachment of aquatic weeds. Aquatic weeds such as Duckweed, Salvinia, Elodea, Potamogeton and the like are hardy weeds which thrive in aqueous environments and tend to spread rapidly choking out the aquatic life in said bodies and clogging the use of said bodies for recreational purposes. Additionally, the rapid spread of such weeds decreases the normal circulation within an aqueous body tending to give rise to stagnation therein with resultant pollution of such bodies. It has been found extremely difficult to develop aquatic herbicides which are both effective herbicidally and yet substantially non-toxic to aquatic life, e.g. fish.

Land used for agronomic purposes is similarly threatened with takeover by weeds. Terrestrial weeds grow quite rapidly and hardily, choking out and overgrowing desirable crops and plants. Moreover, the weeds also give rise to airborne pollen, spores and the like which cause allergic reactions, especially hayfever. In the effort to control these noxious weeds, however, it is quite important that the materials employed exhibit effective herbicidal activity while simultaneously displaying a substantial lack of phytotoxic behavior toward desirable crops and plants.

Effective herbicidal activity can be manifested in several different ways. For example, the herbicide can be applied to the situs to be treated prior to emergence of the weed species sought to be controlled and effect growth retardation or inhibition. Selective herbicidal activity of this type is especially important in areas where useful or desirable plants or vegetation are growing, but where the weeds sought to be controlled have not as yet emerged. Thus, pre-emergence herbicidal activity is primarily directed at thwarting weed growth. Herbicidal activity can also be manifested upon application to the weeds sought to be controlled after they have emerged. On such post-emergence basis, herbicidal activity can be obtained by compounds which selectively burn or cause contact injury to the weeds resulting in the ultimate eradication thereof. Alternatively, weeds can be killed by effecting chlorosis and ultimate necrosis of some of the plant tissue leading to the death of the weeds. Still further, herbicides can cause growth retardation or a combination of any of the above such as burning the plant foliage and simultaneously or thereafter retarding the plant growth. Plant hormones or growth regulators can also be herbicides.

Thus, it can be seen that both aquatic and terrestrial weeds are noxious plants and much effort has been devoted to their selective eradication without commensurate damage to aquatic life or useful or desirable plants and vegetation.

Accordingly, it is an object of the present invention to provide effective herbicidal compositions which display remarkable selectivity for aquatic and/or terrestrial weeds while simultaneously demonstrating substantially no harmful effects towards either aquatic life in the aqueous bodies or useful or desirable plants and vegetation growing in areas in which the herbicide is applied.

These as well as other objects are accomplished by the present invention which is based upon the surprising discovery that compounds containing the 1-anthraquinonyloxy structure:

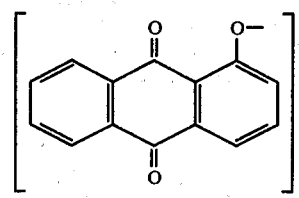

when applied to the situs to be treated provide an exceptionally high degree of control over the growth of weeds.

As employed herein, the term "pre-emergence" is meant to denote that the compound is applied to the situs to be treated prior to emergence of the weed species sought to be controlled. This term, as used herein, also means the application of herbicidal compounds falling within the scope of the present invention to areas wherein useful or desirable plants or vegetation are growing, but where the weeds sought to be controlled have not as yet emerged.

As employed herein, the term "post-emergence" is intended to denote that the compound is applied to the weeds sought to be controlled after they have emerged and are in an active state of growth. This term is also used to describe the application of herbicidally active compounds of the present invention to areas in and around the growing weeds sought to be controlled for purposes of effecting root absorption in the undesirable weeds species.

In accordance with the present invention, it has been found that compounds containing the 1-anthraquinonyloxy moiety demonstrate commercially useful and remarkable herbicidal properties while simultaneously displaying substantially no adverse effect on aquatic life or phytotoxic behavior toward desirable or useful crops and plants.

The compounds of the present invention have been found to provide substantially complete control of aquatic weeds such as Duckweed, Salvinia, Elodea, Potamogeton and the like when applied in concentrations ranging from about 0.1 part to about 25 parts per million parts water. Generally, it is considered preferable to apply these compounds in concentrations ranging from about 0.5 part to about 12 parts per million parts water.

The compounds of the present invention have also been found to display herbicidal properties with respect to terrestrial weeds on a pre-emergence and/or post-emergence basis depending upon the concentration used, the formulation employed and the type of weed species treated. The compounds of the present invention have been found to be effective herbicides for such terrestrial weeds as cheat grass, barnyard grass, pigweed, nutsedge, lambsquarter, crab grass, downy brome, Johnson grass, mustard, foxtail grass and the like, while exhibiting substantially no untoward effects on useful crops such as corn, snapbeans and the like, when applied in concentrations ranging from about 0.1 pound to about 16 pounds per acre. The compounds of this invention are capable of causing necrosis in such weeds as barnyard grass, foxtail grass, lambsquarter, crab grass and the like; of retarding the growth of Johnson grass, crab grass, foxtail grass and the like; of burning barnyard grass, mustard, crab grass and the like.

The herbicidally effective compounds of the present invention are those which contain the 1-anthraquinonyloxy moiety. For example, the growth of weeds can be controlled by applying to the situs to be treated, an effective herbicidal amount of compounds containing the 1-anthraquinonyloxy moiety such as those having the structural formula:

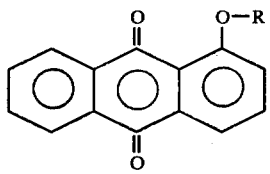

wherein R is selected from the group consisting of hydrogen, aliphatic, aromatic and acyl radicals. As employed herein, these radicals are to be broadly construed to include substituted derivatives thereof.

More specifically, compounds encompassed by the present invention are compounds such as those represented by the structural formula:

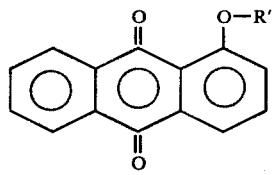

wherein R' is selected from the group consisting of hydrogen, alkyl containing from 1 to about 8 carbon atoms, alkenyl containing from 2 to about 4 carbon atoms, alkynyl containing from 2 to about 4 carbon atoms,

and [Ar]($R'''$)$_n$, with R'' being selected from the group consisting of alkyl containing from 1 to about 8 carbon atoms, alkoxy containing from 1 to about 4 carbon atoms, alkenyl containing from 2 to about 4 carbon atoms, such as allyl, alkynyl containing from 2 to about 4 carbon atoms such as propargyl and —N—(R'''')$_2$ wherein each R'''' is independently selected from the group consisting of hydrogen, alkyl, aryl or when taken together with the nitrogen form a 5 or 6 membered heterocyclic moiety; [Ar] is an aryl moiety of 6 to 12 carbon atoms such as phenyl, biphenyl and naphthyl; and R''' is a member selected from the group consisting of alkyl containing from 1 to about 8 carbon atoms, nitro, sulfonyl, sulfamyl, sulfinyl, sulfo and halo radicals, and n is a number ranging from 0 to 3.

Illustrative of the compounds containing the 1-anthraquinonyloxy moiety which have been found useful in accordance with the present invention are compounds such as 1-hydroxyanthraquinone, 1-acetoxy anthraquinone, 1-phenoxy anthraquinone, 1-(4-nitrophenoxy)-anthraquinone, 1-(2,4-dinitrophenoxy)anthraquinone, 1-chloroacetoxy-anthraquinone, 1-anthraquinonyl isopropyl carbonate, 1-anthraquinonyl dimethyl carbamate, 1-(4-ethylsulfamyl phenoxy)-anthraquinone, 1-(4-diethylsulfamylphenoxy)-anthraquinone, 1,8-dihydroxyanthraquinone, 1-anthraquinonyl diethylcarbamate, 1-(4-chlorosulfonylphenoxy)-anthraquinone, 1-(2,4-dichlorophenoxy)-anthraquinone, 1-($\alpha^2,\alpha^4$-dichloro-2,4-xylyloxy)-anthraquinone, 1-(4-methoxysulfonylphenoxy)-anthraquinone, 1-(4-chlorophenoxy)-anthraquinone, 1,1'-[4-(1-anthraquinonyloxy)-m-phenylenedimethylene]-di-pyridinium chloride, 6-(1-anthraquinonyloxy)-meta-toluene sulfonic acid sodium salt, 4-(1-anthraquinonyloxy)-benzene sulfinic acid, 1-anthraquinonyl diphenylcarbamate, 1-anthraquinonyl N-methyl-N-phenylcarbamate, 1-hydroxy-4-methyl-anthraquinone, 1-anthraquinonyloxy acetic acid, 1-anthraquinonyl-2,3-dichloroacrylate, 1-(4-sulfamylphenoxy)anthraquinone, 1-(p-tolyloxy)-anthraquinone, ethyl (1-anthraquinonyloxy) acetate, 1-anthraquinonyl piperidinylcarbamate and the like.

Certain classes of compounds containing the 1-anthraquinonyloxy moiety are novel. Thus, compounds having the structural formula:

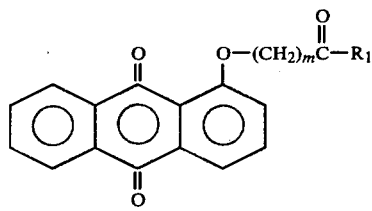

wherein $R_1$ is a member selected from the group consisting of alkoxy containing from 1 to about 8 carbon atoms, haloalkoxy, hydroxy, alkenyloxy containing from 2 to about 4 carbon atoms, alkynyloxy containing from 2 to about 4 carbon atoms and —N($R_2$)$_2$ wherein each $R_2$ is independently selected from the group consisting of hydrogen, alkyl, aryl or when taken together with the nitrogen form a 5 or 6 membered heterocyclic moiety, and m is a number from 0 to 1.

Generally, these novel compounds are carbonate, carbamate, and acetic acid or acetic acid ester derivatives of the 1-anthraquinonyloxy moiety. The carbonates of this class are represented by the structural formula:

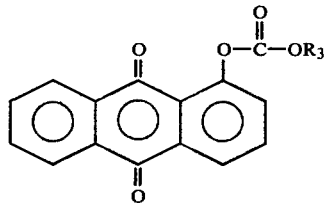

wherein $R_3$ is an alkyl or haloalkyl containing from 1 to about 8 carbon atoms, and can be illustrated, for example, by 1-anthraquinonyl isopropylcarbonate, 1-anthraquinonyl chloroethylcarbonate, 1-anthraquinonyl ethylcarbonate and the like. The carbamates are represented by the structural formula:

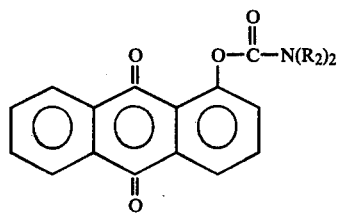

wherein each $R_2$ is independently selected from the group consisting of hydrogen, alkyl, aryl or when taken together with the nitrogen form a 5 or 6 membered heterocyclic moiety, and are illustrated, for example, by 1-anthraquinonyl dimethylcarbamate, 1-anthraquinonyl diphenylcarbamate, 1-anthraquinonyl N-methyl, N-phenylcarbamate, 1-anthraquinonyl piperidinylcarbamate and the like. The acetic acid and acetic acid esters are represented by the structural formula:

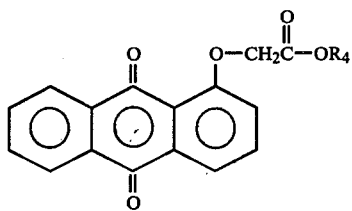

wherein $R_4$ is hydrogen or alkyl of 1 to about 8 carbon atoms, and are illustrated, for example, by 1-anthraquinonyloxy acetic acid and ethyl (1-anthraquinonyloxy) acetate.

The compounds of the present invention can be prepared from known compounds which, in many cases, are commercially available, such as 1-chloroanthraquinone or 1-hydroxyanthraquinone.

1-Hydroxyanthraquinone is a known compound which can be obtained by several conventional techniques, for example, it can be obtained from 1-anthraquinonesulfonic acid by simply heating with alkali carbonates in aqueous solution under pressure. Alkali metal salts of 1-anthraquinonesulfonic acid can also be converted to the hydroxy derivative by heating with aqueous solutions of alkali metal and alkaline earth metal hydroxides. Upon acidification of the resulting reaction medium with an acid such as sulfuric acid, the 1-hydroxyanthraquinone precipitates in quite pure form. Alternatively, 1-hydroxyanthraquinone can be obtained directly from 1-anthraquinonesulfonic acid by treatment with water or dilute sulfuric acid in an autoclave at 200° to 300° C. Employing the above processes as well as other known processes for the preparation of 1-hydroxyanthraquinone, the compound can be obtained in crystalline form as pale yellow to orange needles having a melting point of about 190° C. The compound is insoluble in water, but is soluble in alcohols and organic solvents such as ethanol, propylene glycol, acetone, N-methyl pyrrolidone and the like.

The novel carbonate derivatives of the present invention can be prepared by a condensation reaction between 1-hydroxyanthraquinone and a suitable chlorocarbonate such as, for example, isopropyl chlorocarbonate, to form the desired 1-anthraquinonyl isopropyl carbonate. The desired chlorocarbonate is readily prepared by reaction of phosgene and an alcohol. The novel carbamate derivatives of the present invention are similarly prepared by condensation of 1-hydroxyanthraquinone with a carbamyl chloride. Thus, for example, 1-anthraquinonyl dimethyl carbamate can be prepared by reaction between 1-hydroxyanthraquinone and dimethyl carbamyl chloride. Similarly, the novel acetic acid ester derivatives can be obtained by reaction of 1-hydroxyanthraquinone with the desired ester of acetic acid such as ethyl chloroacetate or ethyl bromoacetate. The acetic acid derivative can be obtained from the ester by hydrolysis. Other compounds containing the 1-anthraquinonyloxy moiety can be prepared from 1-hydroxyanthraquinone, 1-chloroanthraquinone or other similar anthraquinone starting materials employing conventional organic synthesis techniques. Generally, these reactions occur in substantially equimolar proportions. If desired, however, quantities in excess of the stoichiometric proportions can be employed.

The anthraquinone derivatives of the present invention are not appreciably water soluble except for the derivatives containing the sodium salts of sulfonic acid or quaternary salts; however, the herbicidal compositions of the present invention can be applied to the situs to be treated in admixture with a suitable inert vehicle. For example, the herbicide can be applied as an aqueous dispersion, as an alcoholic or acetone or other hydrocarbon solvent/water mixture, as an emulsion or as a powder in combination with a suitable granular vehicle such as diatomaceous earth, talc, calcium sulfate, vermiculite, clay and the like. If desired, suitable emulsifiers, surfactants, dispersing agents, extenders and the like can also be employed. Generally, it is considered preferable to apply the herbicide as a dispersion wherein the 1-anthraquinonyloxy-containing compound is dissolved in a suitable solvent such as acetone and then applied as an aqueous dispersion in concentrations ranging from about 0.1 part to about 25 parts per million parts of water. Application of the herbicidal compositions can be made on either a pre-emergence or post-emergence basis; however, post-emergence application is generally considered preferably for optimum activity. Although the preferred method of application of the compounds of this invention is directly to the foliage and stems of the weeds, it has been found that such compounds may be applied to the soil or aqueous body in which the plants are growing, and that such compounds will be root-absorbed to a sufficient extent so as to result in plant responses in accordance with the teachings of this invention.

The following examples further illustrate the present invention. These examples are included herewith solely by way of illustration and are not intended in any way to be construed as a limitation of this invention. Unless otherwise stated, all percentages and parts are by weight.

EXAMPLE 1

A mixture of 22.4 gms. (0.1 mole) of 1-hydroxyanthraquinone, 350 cc. of acetone, 10.1 gms. (0.1 mole) triethylamine and 12.3 gms. (0.1 mole) isopropyl chlorocarbonate (prepared by reaction of phosgene with isopropyl alcohol) was heated to reflux and allowed to reflux for 4 hours. The reaction mixture was cooled and filtered to remove a mixture of amine hydrochloride and unreacted anthraquinone. A small amount of water was added to the filtrate which was then cooled to recover the crude product. The product was recrystallized from methanol to yield 10.1 gms. of 1-anthraquinonyl isopropyl carbonate having a melting point of 147°–152° C. Elemental analysis showed:

|  |  | Calcd. | Found |
|---|---|---|---|
| $C_{18}H_{14}O_5$ | % C | 69.7 | 70.2 |
| Molecular weight 310 | % H | 4.5 | 4.67 |

EXAMPLE 2

Employing the same procedure as described in Example 1, 1-anthraquinonyl chloroethyl carbonate was prepared by reacting 1-hydroxyanthraquinone with chloroethyl chlorocarbonate. The compound exhibited a melting point of 138°–143° C. Elemental analysis showed:

|  |  | Calcd. | Found |
|---|---|---|---|
| $C_{17}H_{11}Cl\,O_5$ | % C | 61.7 | 61.73 |
| Molecular weight 330.5 | % H | 10.74 | 10.69 |
|  | % Cl | 3.35 | 3.51 |

EXAMPLE 3

Employing substantially the same procedure as in Example 1, 1-anthraquinonyl ethyl carbonate having a melting point of 170°–172° C. was prepared by reaction of 1-hydroxyanthraquinone and ethyl chlorocarbonate.

EXAMPLE 4

A mixture of 2.24 gms. (0.01 mole) 1-hydroxyanthraquinone, 3.0 ml. pyridine and 1.1 gms. (0.01 mole) dimethyl carbamyl chloride was heated to 150° C. for 2 hours in an oil bath. The resulting mixture was slurried with dilute HCl, filtered and washed with water. The crude product was recovered and recrystallized from 95% ethanol. Recrystallization was repeated to yield 1.8 gms. of 1-anthraquinonyl dimethyl carbamate having a melting point of 196°–199° C. Mixed melting point with 1-hydroxyanthraquinone (m.p. 193°–195° C.)=165°–181° C. Elemental analysis showed:

|  |  | Calcd. | Found |
|---|---|---|---|
| $C_{17}H_{13}N\,O_4$ | % N | 4.75 | 4.35 |

EXAMPLE 5

Employing the same procedure as described in Example 4, diethylcarbamyl chloride, diphenylcarbamyl chloride, ethylcarbamyl chloride and N-methyl, N-phenyl carbamyl chloride were respectively reacted with 1-hydroxyanthraquinone in pyridine to obtain the corresponding 1-anthraquinonyl carbamate derivatives.

EXAMPLE 6

The following example illustrates the preparation of 1-anthraquinonyl piperidinylcarbamate.

In a 500 cc. 4-neck flask fitted with stirrer, thermometer, gas inlet tube and dry ice filled condenser was placed 100 cc. ethyl acetate. Phosgene was bubbled in at room temperature until a saturated solution was obtained. Forty-seven grams of $COCl_2$ were absorbed. At this point, 56 cc. piperidine (0.555 moles) was added dropwise to the solution accompanied by the simultaneous addition of phosgene. The temperature was maintained at 30°–40° C. with an ice bath. A total of 148 g. of phosgene was added. The temperature was raised to 50° C. to drive off excess $COCl_2$. After standing overnight the solution was distilled; the fraction boiling at 170°–171° C. at 0.3 mm. pressure was collected and represented the desired carbamyl chloride.

To a stirred solution of 60 cc. anhydrous pyridine containing 8.96 grams (0.04 moles) of 1-hydroxyanthraquinone was added 17.8 g. piperidinyl carbamyl chloride. The solution was heated at reflux 116° C. for 8 hours, then cooled to room temperature. The reaction mixture was drowned in 600 cc. 5% HCl, and the solid precipitate was collected by filtration followed by washing with dilute HCl and then water. The dry weight of the crude carbamate was 12.8 g. melting at 156°–159° C. The collected solid was crystallized from 250 cc. ethanol giving a dry weight of 10.3 g. melting at 166°–168° C. Nitrogen analysis of the purified compound was 3.98% versus a theoretical value of 4.18%. The compound was not soluble in hot dilute sodium hydroxide in contrast to 1-hydroxyanthraquinone. The new compound was readily soluble in its reduced form in aqueous sodium hydrosulfite-sodium hydroxide solution.

EXAMPLE 7

The following example illustrates the preparation of ethyl (1-anthraquinonyloxy) acetate.

In a 500 cc. three-necked flask equipped with stirrer, thermometer and condenser was charged 22.4 g. (0.10 mole) 1-hydroxyanthraquinone and 100 cc. N-methylpyrrolidone. At 25° C., 5.4 g. sodium methylate (0.10) was added, and the stirred solution was warmed to 85°–90° C. on a steambath. On cooling to 48° C., 16.7 g. of ethyl bromoacetate was added. The temperature of the solution was held at 70° C. for 3 hours. Color changes from deep purple to dark-red brown to dull brown were noted. The reaction mixture stood overnight at room temperature and was then diluted with 300 cc. water. After stirring for several hours the precipitate which formed was isolated by filtration and washed with dilute sodium hydroxide (1.0 g. NaOH in 250 cc.) $H_2O$. The precipitate was further washed until colorless. A dry weight of 29.4 g. of product was obtained. It was crystallized from ethanol and melted at 173°–175° C. The golden yellow crystals analyzed as follows:

|  | Calcd. | Found |
|---|---|---|
| % H | 4.52 | 4.77 |
| % C | 69.9 | 69.7 |

EXAMPLE 8

The following example illustrates the preparation of 1-anthraquinonyloxy acetic acid.

In a stirred flask fitted with condenser and thermometer was charged a solution consisting of 350 cc. ethanol, 150 cc. $H_2O$, and 40 g. KOH. To the solution was added 10.0 g. of the ethyl ester of 1-anthraquinonyl acetic acid. The solution was brought to reflux on a steambath. An additional amount of 310 cc. $H_2O$ and 240 cc. ethanol was added. After refluxing 1 hour, the solution was cooled to 50° C., and 50 cc. of 37% HCl was slowly dropped in. The desired acid precipitated and was stirred at room temperature for several hours. The pale yellow precipitate was removed by filtration and washed free of acid. A dry weight of 8.0 g. was obtained melting at 245°–247° C. The compound was soluble in hot dilute sodium bicarbonate solution.

The following examples illustrate the herbicidal activity of compounds containing the 1-anthraquinonyloxy moiety with respect to a wide variety of aquatic weeds and terrestrial weeds. As to the latter, herbicidal activity is shown both on a pre-emergence and post-emergence basis.

In the data presented below, either a numeric or alpha-numeric rating is given to express the degree of response and type of activity noted. The numerical rating goes from "0" for no visible response to "10" for a maximum response for the particular type of activity. Different types of activity are identified by code letters set forth below. Since a particular compound can cause several different biological effects on the same plant, the alpha-numeric system employed enables a composite picture of activity and response to be succinctly stated for each compound with respect to each weed tested.

The following is a key to the code letters employed:

| Code Letter | Meaning |
| --- | --- |
| A | Growth accelerated |
| B | Burn or contact injury - indicating an acute response within 48 hours after treatment. A 5 rating would indicate that the plant was half dead and a 10 would indicate that the plant was completely dead. |
| C or N | Chlorosis (C) to necrosis (N) (dieback) to death. This indicates a chronic response taking place over a period of time. It indicates that the compound at first caused chlorosis, then necrosis of some of the tissues and finally death of the plant. Examples of this type of rating: 1–3 = increasing degrees of chlorosis; 4–8 = increasing amounts of necrostic tissue; 9 = all tissues dead except part of stem; 10 = plant completely dead. |
| E | Emergence inhibited. A rating of 5 means only half of the seedlings emerged as compared to the control. |
| R | Growth retarded. A rating of 5 indicates that the plants were half the size of the controls. |
| D | Indicates that flowering was delayed or inhibited. |
| K | Axillary stimulation - indicates axillary bud growth. |
| P | Unusual pigmentation - a change in coloration of the plant such as a darker green color. |
|  | A rating of zero (0) by itself indicates that the compound had no visible effects on that plant species. |
| n.t. | Compound not tested for that particular plant species. |

EXAMPLES 9–50

The following examples, a wide variety of compounds containing the 1-anthraquinonyloxy moiety were applied respectively to aquatic weeds in an active state of growth. The aquatic weeds were growing under aquatic conditions in a greenhouse. The compounds were dissolved in 5 ml. of acetone and applied in an aqueous spray in a concentration of 5 parts compound per million parts of water. Approximately 3 weeks after spray application, the treated weeds were inspected and the results are reported below in Table I.

The results obtained demonstrate the remarkable effectiveness of compounds containing the 1-anthraquinonyloxy moiety as herbicides for aquatic weeds.

TABLE I

AQUATIC WEED CONTROL

| Example # | | Duckweed | Salvinia | Elodea | Potamogeton |
| --- | --- | --- | --- | --- | --- |
| 9 | 1-hydroxyanthraquinone | 10 | 10 | 10 | 10 |
| 10 | 1-acetoxy anthraquinone | 10 | 10 | 10 | 10 |
| 11 | 1-phenoxy anthraquinone | 10 | 10 | 10 | 10 |
| 12 | 1-(4-nitrophenoxy)-anthraquinone | 6 | 10 | 10 | 0 |
| 13 | 1-(2,4-dinitrophenoxy) anthraquinone | 0 | 10 | 6 | 0 |
| 14 | 1-anthraquinonyloxy chloroacetate | 0 | 0 | 0 | 6 |
| 15 | 1-hydroxyanthraquinone isopropylcarbonate | 10 | 10 | 10 | 10 |
| 16 | 1-hydroxyanthraquinone dimethylcarbamate | 10 | 10 | 10 | 10 |
| 17 | 1-(4-ethylsulfamyl phenoxy)-anthraquinone | 9 | 10 | 10 | 10 |
| 18 | 1-(4-diethylsulfamyl phenoxy)-anthraquinone | 3 | 10 | 10 | 10 |
| 19 | 1-hydroxyanthraquinone diethylcarbamate | 10 | 10 | 10 | 10 |
| 20 | 4-(1-anthraquinonyloxy)-benzene sulfonyl chloride | 10 | 10 | 10 | 10 |
| 21 | 1-(2,4-dichlorophenoxy) anthraquinone | 3 | 9 | 10 | 0 |
| 22 | 1($\alpha^2,\alpha^4$-dichloro-2,4-xylyloxy)-anthraquinone | 0 | 10 | 9 | 3 |
| 23 | 1-(4-methyloxysulfonyl phenoxy)-anthraquinone | 3 | 10 | 10 | 3 |
| 24 | 1-(4-chlorophenoxy)-anthraquinone | 0 | 10 | 9 | 10 |
| 25 | 1,1'[4-(1-anthraquinonyloxy) m-phenylene dimethyl]di pyridinium chloride) | 10 | 10 | 10 | 10 |
| 26 | 6-(1-anthraquinonyloxy)meta-toluene sulfonic acid sodium | 6 | 10 | 10 | 0 |

TABLE I-continued
AQUATIC WEED CONTROL

| Example # | | Duckweed | Salvinia | Elodea | Potamogeton |
|---|---|---|---|---|---|
| | salt | | | | |
| 27 | 4-(1-anthraquinonyloxy) benzene sulfinic acid | 10 | 10 | 10 | 10 |
| 28 | 1-hydroxyanthraquinone diphenylcarbamate | 0 | 10 | 9 | 10 |
| 29 | 1-hydroxyanthraquinone N—methyl-N—phenylcarbamate | 0 | 10 | 10 | 10 |
| 30 | 1-hydroxy-4-methyl-anthraquinone | 10 | 10 | 10 | 10 |
| 31 | 1-anthraquinonyloxy acetic acid | 0 | 10 | 10 | 0 |
| 32 | 1-anthraquinonyl chloroethylcarbonate | 3 | 10 | 10 | 10 |
| 33 | 1-anthraquinonyl-2,3-dichloroacrylate | 3 | 9 | 10 | 6 |
| 34 | 1-anthraquinonyl ethyl carbonate | 9 | 10 | 10 | 6 |
| 35 | 1-(4-sulfamylphenoxy) anthrquinone | 9 | 10 | 10 | 10 |
| 36 | 4-(1-anthraquinonyloxy) benzene sulfonic acid sodium salt | 9 | 10 | 10 | 10 |
| 37 | 1-tolyloxy anthraquinone | 10 | 10 | 10 | 10 |
| 38 | 4-(1-anthraquinonyloxy)-3-nitrotoluene | 0 | 10 | 10 | 1 |
| 39 | 4-(1-anthraquinonyloxy)-3,5-dichlorotoluene | 9 | 10 | 10 | 10 |
| 40 | 4-(1-anthraquinonyloxy)-3-chlorotoluene | 9 | 10 | 10 | 2 |
| 41 | 6-(1-anthraquinonyloxy)-meta-toluene sulfonyl chloride | 9 | 10 | 10 | 9 |
| 42 | 4-(1-anthraquinonyloxy)-3-diethylsulfamyl toluene | 3 | 10 | 10 | 0 |
| 43 | 6-(1-anthraquinonyloxy)-meta-chlorobenzene sulfonyl chloride | 10 | 10 | 10 | 10 |
| 44 | 4-(1-anthraquinonyloxy)-3-sulfamyl-chlorobenzene | 6 | 10 | 6 | 10 |
| 45 | 4-(1-anthraquinonyloxy)-3-ethylsulfamyl-chlorobenzene | 6 | 10 | 6 | 10 |
| 46 | 4-(1-anthraquinonyloxy)-3-diethylsulfamyl-chlorobenzene | 6 | 10 | 10 | 10 |
| 47 | 4-(1-anthraquinonyloxy)-3-N—phenyl sulfamyl-chlorobenzene | 6 | 10 | 6 | 10 |
| 48 | 1-anthraquinonyl, N—methyl-N—phenylcarbamate | 0 | 10 | 10 | 10 |
| 49 | 1-anthraquinonyl pyridinyl-carbamate | 10 | 10 | 10 | 10 |
| 50 | ethyl (1-anthraquinonyloxy) acetate | 9 | 10 | 10 | 9 |

EXAMPLE 51

The following example illustrates the criticality of the presence of the 1-anthraquinonyloxy moiety in compounds of the present invention in order for herbicidal activity to be effected. This example also illustrates that as long as the 1-anthraquinonyloxy moiety is present in the compound, the presence of other substituents, either in the same or in different rings, still results in compounds exhibiting effective herbicidal activity.

Employing the identical procedure described in Example 9, the anthraquinone derivatives set forth below were dissolved in 5 ml. acetone and applied to aquatic weeds in an active state of growth as an aqueous spray in a concentration of 5 parts compound per million parts of water. About 3 weeks after spray application, the treated weeds were inspected and compared with untreated or control areas. The results obtained are reported in Table II below.

TABLE II

| Compound | % Control of Weeds | | | |
|---|---|---|---|---|
| | Duckweed | Salvinia | Elodea | Potamogeton |
| 1-hydroxyanthraquinone | 10 | 10 | 10 | 10 |
| 2-hydroxyanthraquinone | 0 | 0 | 0 | 0 |
| 1,8-dihydroxyanthraquinone | 0 | 7 | 9 | 2 |

TABLE II-continued

| Compound | % Control of Weeds | | | |
|---|---|---|---|---|
| | Duckweed | Salvinia | Elodea | Potamogeton |
| 1-hydroxy-2-methyl anthraquinone structure | 10 | 10 | 10 | 10 |

The above data clearly demonstrates the surprising necessity for the presence of the 1-anthraquinonyloxy moiety in compounds in order to effect herbicidal activity.

EXAMPLE 52

1-Hydroxyanthraquinone was dissolved in 5 mil. of acetone and the solution was then admixed with water in an aquarium to provide a concentration of 5 ppm of the 1-hydroxyanthraquinone in the water contained therein. Aquatic life such as goldfish, minnows, turtles, snails and the like were added to the aquarium in a good state of health. After three weeks, the aquarium was inspected and the presence of 1-hydroxyanthraquinone was found to exhibit no noticeable effect on the aquatic life.

The foregoing examples clearly demonstrate the high rate of control over aquatic weeds afforded by use of compounds containing the 1-anthraquinonyloxy moiety in accordance with the present invention. Moreover, it has been demonstrated that although these compounds are extremely active aquatic herbicides, they exhibit no noticeable adverse effect on aquatic life.

EXAMPLES 53-61

In the following examples, seeds of a wide variety of weeds were respectively sown in separate soil-containing flats. The seeds were then sprayed with an aqueous spray containing a compound containing the 1-anthraquinonyloxy moiety dissolved in 5 ml. of acetone so as to apply thereto the equivalent of 8 pounds per acre of the compound. Thereafter, the seeds were covered with soil. About three weeks later, the flats were inspected and the treated weeds were compared with untreated or control areas. The results obtained are reported in Table III below.

TABLE III

PRE-EMERGENCE WEED CONTROL

| Example # | 1-anthraquinonyloxy-containing compound | Cheat Grass | Snapbeans | Chickweed | Wild Oats | Barnyard Grass | Foxtail Grass | Morning-Glory | Mustard | Corn | Velvet Leaf | Johnson Grass | Pigweed |
|---|---|---|---|---|---|---|---|---|---|---|---|---|---|
| 53 | 1-hydroxyanthraquinone | 0 | 0 | 0 | 0 | 0 | 0 | 0 | 0 | 0 | 0 | 0 | 0 |
| 54 | 1-acetoxy anthraquinone | 9E 7R | 0 | 0 | .0 | 0 | 0 | 0 | 0 | 0 | 0 | 0 | 0 |
| 55 | 1-phenoxy anthraquinone | 0 | 0 | 0 | 0 | 0 | 0 | 0 | 0 | 0 | 0 | 0 | 10E |
| 56 | 1-(4-nitrophenoxy)-anthraquinone | 0 | 0 | 0 | 0 | 0 | 0 | 0 | 0 | 0 | 0 | 0 | 0 |
| 57 | 1-hydroxyanthraquinone dimethylcarbamate | nt | 0 | 0 | 3C | 5C | 3E 4R | 0 | 0 | 1C | 0 | 3C | 0 |
| 58 | 1-hydroxyanthraquinone diethylcarbamate | nt | 0 | 0 | 0 | 0 | 0 | 0 | 0 | 0 | 0 | 0 | 0 |
| 59 | 6-(1-anthraquinonyloxy)meta-toluene sulfonic acid sodium salt | 0 | 0 | 0 | 0 | 0 | 0 | 0 | 0 | 0 | 0 | 0 | 0 |
| 60 | 4-(1-anthraquinonyloxy)benzene sulfinic acid | nt | 0 | 0 | 0 | 0 | 0 | 0 | 0 | 0 | 0 | nt | 0 |
| 61 | 2-(1-anthraquinonyloxy)acetic acid | nt | 0 | 0 | nt | 4E 5C 7R | 3R | 5E 3R | 0 | 0 | 0 | nt | 0 |

| Example # | 1-anthraquinonyloxy-containing compound | Curled Dock | Nutsedge | Alopecures | Cucumber | Lambsquarter | Crab Grass | Marigold | Teaweed | Downy Brome | Flax | Buckwheat | Mugwort |
|---|---|---|---|---|---|---|---|---|---|---|---|---|---|
| 53 | 1-hydroxyanthraquinone | 0 | 10E | 0 | 0 | 0 | 0 | 0 | nt | nt | nt | nt | nt |
| 54 | 1-acetoxy anthraquinone | 0 | 0 | 0 | 0 | 8R | 9E 6R | 0 | nt | nt | nt | nt | nt |
| 55 | 1-phenoxy anthraquinone | 5E | 0 | 0 | 0 | 0 | 0 | 0 | nt | nt | nt | nt | nt |
| 56 | 1-(4-nitrophenoxy)-anthraquinone | 0 | 0 | 0 | 4C 3R | 9E | 4R | 0 | nt | nt | nt | nt | nt |
| 57 | 1-hydroxyanthraquinone dimethylcarbamate | 0 | 0 | 5E 5C 4R | 2C 3R | nt | 10E | 0 | 0 | 3C | nt | nt | nt |
| 58 | 1-hydroxyanthraquinone diethylcarbamate | 0 | 0 | 0 | 0 | 0 | 10E | 0 | 0 | 0 | nt | nt | nt |
| 59 | 6-(1-anthraquinonyloxy)meta-toluene sulfonic acid sodium salt | 0 | 0 | 0 | 0 | 0 | 10E | 0 | 0 | 0 | nt | nt | nt |
| 60 | 4-(1-anthraquinonyloxy)benzene sulfinic acid | nt | 0 | nt | 0 | nt | 10E | 0 | 0 | 0 | 0 | 0 | 0 |
| 61 | 2-(1-anthraquinonyloxy)acetic acid | nt | 0 | nt | 0 | nt | 9E 7R | 0 | 0 | 0 | 0 | 0 | 0 |

The foregoing examples demonstrate the selective effectiveness of the compounds of the present invention on a pre-emergence basis. The growth of noxious weeds such as crab grass is severely retarded whereas the growth of beneficial crops is substantially unaffected.

EXAMPLES 62-83

In the following examples, seeds of a wide variety of weeds were respectively sown in separate soil-containing flats and were allowed to grow under greenhouse conditions for about two weeks. At this time, the weeds were in an active state of growth. The weeds were then sprayed with an aqueous spray containing a compound containing the 1-anthraquinonyloxy moiety dissolved in 5 ml. of acetone so as to apply thereto the equivalent of 8 pounds per acre of the compound. About three weeks later, the flats were inspected and the treated weeds were compared with untreated or control areas. The results obtained are reported in Table IV below.

TABLE IV

| | | | | | | | | | | | | |
|---|---|---|---|---|---|---|---|---|---|---|---|---|
| POST-EMERGENCE WEED CONTROL | | | | | | | | | | | | |
| Example # | 1-anthraquinonyloxy-containing compound | Cheat Grass | Snap-beans | Chick-weed | Wild Oats | Barnyard Grass | Foxtail Grass | Morning-Glory | Mus-tard | Corn | Velvet Leaf | Johnson Grass | Pig-weed |
| 62 | 1-hydroxy anthraquinone | 0 | 0 | 0 | 0 | 0 | 0 | 0 | 0 | 0 | 3R | 0 | 2R |
| 63 | 1-acetoxy anthraquinone | 0 | 2A | 0 | 0 | 0 | 9N 7R | 0 | 2C | 1C | 0 | 0 | 9N |
| 64 | 1-phenoxy anthraquinone | 2C | 3C | 2R | 1N 3C | 9N | 9N 7R | 4N | 10N | 2N | 1N 2C | 9N | 9N 4R |
| 65 | 1-(4-nitrophenoxy)-anthraquinone | 0 | 1N | 0 | 0 | 4N | 9N 5R 3C | 0 | 9N | 0 | 0 | 9N 7R | 10N |
| 66 | 1-(2,4-dinitrophenoxy anthraquinone) | 0 | 0 | 0 | 0 | 9N 9R | 10N | 0 | 0 | 0 | 0 | 8N 3C 9R | 6N |
| 67 | 1-anthraquinonyloxy chloroacetate | nt | 1N | 6N | 2N | 10N | 10N | 10N | 7N | 2N | 0 | 10N | 10N |
| 68 | 1-hydroxyanthraquinone isopropyl carbonate | nt | 1N | 0 | 2N | 10N | 10N | 1N | 3N 3R | 2C | 0 | 8N 7R | 10N |
| 69 | 1-(4-ethylsulfamyl phenoxy)-anthraquinone | nt | 2B | 3B | 2B | 3B | 0 | 0 | 0 | 1B | 0 | 0 | 0 |
| 70 | 1-(4-diethylsulfamyl phenoxy)-anthraquinone | nt | 1B 1C | 0 | 2B | 2B | 8B 3R | 0 | 0 | 0 | 0 | 7B | 8B 5R |
| 71 | 1-hydroxyanthraquinone diethylcarbamate | nt | 2B | 7B | 1B | 10B | 10B | 10B | 10B | 1B | 2C 3R | 9B 6C 9R | 10B |
| 72 | 4-(1-anthraquinonyloxy)-benzene sulfonyl chloride | nt | 3B 2R | 3B | 1B | 10B | 9B 9R | 0 | 9B | 2B | 7B 5R | 6B 4C 7R | 8B |
| 73 | 1-(2,4-dichlorophenoxy)anthraquinone | nt | 2B | 0 | 0 | 9B 8R | 8B 6R | 0 | 2B | 1B | 0 | 5B 4R | 10B |
| 74 | 1-(α²,α⁴-dichloro-2,4-xylyloxy)-anthraquinone | nt | 2R | 0 | 0 | 3B | 6B 4R | 0 | 1C | 0 | 0 | 5B 2C 3R | 0 |
| 75 | 1-(4-methyloxysulfonyl phenoxy)-anthraquinone | nt | 2B | 0 | 2B | 10B | 10B | 10B | 10B | 2B | 5B 3R | 10B | 8B |
| 76 | 1-(4-chlorophenoxy)-anthraquinone | nt | 0 | 0 | 0 | 10B | 10B | 8B 3C 4R | 7B 6R | 2B | 5R | 10B | 3B 5R |
| 77 | 1,1'[4-(1-anthraquinonyloxy)M—phenylene dimethyl]di pyridinium chloride) | nt | 0 | 4B 5R | 0 | 7B 4C 6R | 10B | 9B 4C 5R | 0 | 1B | 6B 5R | 7B | 9B 9R |
| 78 | 6-(1-anthraquinonyloxy)meta-toluene sulfonic acid sodium salt | nt | 1N | 1N | 4N | 0 | 0 | 9N 9R | 9N 7R | 1N | 0 | 5N | 0 |
| 79 | 4-(1-anthraquinonyloxy)benzene sulfinic acid | nt | 2B 1K | 7B | 0 | 0 | 3B | 7B | 10B | 0 | 0 | nt | 10B |

| Example # | 1-anthraquinonyloxy-containing moiety | Cheat Grass | Snap-beans | Chick-weed | Wild Oats | Barnyard Grass | Foxtail Grass | Morning-Glory | Mus-tard | Corn | Velvet Leaf | Johnson Grass | Pig-weed |
|---|---|---|---|---|---|---|---|---|---|---|---|---|
| 80 | 1-hydroxyanthraquinone diphenylcarbamate | nt | 1B | 0 | 1B | 5B | 3B 2C | 0 | 0 | 1B | 0 | nt | 3B |
| 81 | 1-hydroxyanthraquinonyloxy N—methyl-N—phenyl carbamate | nt | 3B 2R | 0 | 2B | 5B 3C | 9B 4R | 1B | 3B | 1B | 2B | nt | 10B |
| 82 | 1-hydroxy-4-methyl-anthraquinone | nt | 9B 8R | 3R | 0 | 9B 9R | 2C | 9B 8R | 10B | 1B | 10B | nt | 10B |
| 83 | (1-anthraquinonyloxy)-acetic acid | nt | 4B | 9B | 2B | 9B 10R | 10B | 10B | 10B | 2B | 10B | nt | 10B |

| Example # | 1-anthraquinonyloxy-containing compound | Curled Dock | Nut-sedge | Alope-cures | Cucumber | Lambs-quarter | Crab Grass | Mari-gold | Tea-weed | Downy Brome | Flax | Buck-wheat | Mug-wort |
|---|---|---|---|---|---|---|---|---|---|---|---|---|---|
| 62 | 1-hydroxy anthraquinone | 0 | 0 | 0 | 5R 2P | 10N | 0 | 3R | nt | nt | nt | nt | nt |
| 63 | 1-acetoxy anthraquinone | 0 | 0 | 0 | 2R | 10N | 9N 5C 4R | 3N 5R 10D | nt | nt | nt | nt | nt |

TABLE IV-continued
POST-EMERGENCE WEED CONTROL

| # | 1-anthraquinonyloxy-containing moiety | | | | | | | | | | | | |
|---|---|---|---|---|---|---|---|---|---|---|---|---|---|
| 64 | 1-phenoxy anthraquinone | 0 | 0 | 3C | 2C | 10B | 10B | 3C 7N 3C 3R 10D | nt | nt | nt | nt | nt |
| 65 | 1-(4-nitrophenoxy)-anthraquinone | 0 | 0 | 0 | 3R 2C | 9N 9R | 10N | 9N 5R 10D | nt | nt | nt | nt | nt |
| 66 | 1-(2,4-dinitrophenoxy anthraquinone) | 0 | 5C | 6N 5R | 1N 5R | nt | nt | nt | 8R | 10N 8N 3R 10D | nt | nt | nt |
| 67 | 1-anthraquinonyloxy chloroacetate | 5N | 0 | 4N 3R | 10N | nt | nt | 10N | 10N | 10N | 0 | nt | nt |
| 68 | 1-hydroxyanthraquinone isopropyl carbonate | 0 | 0 | 0 | 5N 6R | nt | nt | 10N | 10N | 10N | 0 | nt | nt |
| 69 | 1-(4-ethylsulfamyl phenoxy)-anthraquinone | 0 | 0 | 0 | 2B | nt | 5B 2C 5R | 5B 2C 4R 4D | 0 | 2B | nt | nt | nt |
| 70 | 1-(4-diethylsulfamyl phenoxy)-anthraquinone | 2B | 0 | 0 | 2B 1C | nt | 8B 4C 9R | 5B 3R 3D | nt | 5B | nt | nt | nt |
| 71 | 1-hydroxyanthraquinone diethylcarbamate | 0 | 0 | 10B | 9B | nt | 10B | 10B | nt | 6B | nt | nt | nt |
| 72 | 4-(1-anthraquinonyloxy)-benzene sulfonyl chloride | 0 | 0 | 5B 4R | 7B 4R | nt | 7B 2C | 7B 4R 4D | nt | 5B | nt | nt | nt |
| 73 | 1-(2,4-dichlorophenoxy)anthraquinone | 0 | 0 | 3B | 6B 8R | nt | 10B | 10B | 10B | 0 | nt | nt | nt |
| 74 | 1-($\alpha^2,\alpha^4$-dichloro-2,4-xylyloxy)-anthraquinone | 0 | 0 | 0 | 2B 2C 6R | nt | 9B 3C 8R | 4B 2C 3R 3D | 0 | 0 | nt | nt | nt |
| 75 | 1-(4-methyloxysulfonyl phenoxy)-anthraquinone | 0 | 0 | 5B 3C | 7B 7R | nt | 10B | 8B 4R 10D | 10B | 3B 4R 10D | nt | nt | nt |
| 76 | 1-(4-chlorophenoxy)-anthraquinone | 0 | 0 | 0 | 9B 8R | nt | 10B | 10B | nt | 0 | nt | nt | nt |
| 77 | 1,1'[4-(1-anthraquinonyloxy)M—phenylene dimethyl]di pyridinium chloride) | 0 | 0 | 0 | 1B 3R | nt | 10B | 1B 6R 10D | nt | 0 | nt | nt | nt |
| 78 | 6-(1-anthraquinonyloxy)meta-toluene sulfonic acid sodium salt | 0 | 0 | 0 | 7N 6R | nt | 10N | 3R 10D | 0 | 0 | nt | nt | nt |
| 79 | 4-(1-anthraquinonyloxy)benzene sulfinic acid | nt | 0 | nt | 4B 6R | nt | 0 | 8B 4R 3D | 0 | 0 | 6B | 0 | 0 |

| Example # | 1-anthraquinonyloxy-containing moiety | Curled Dock | Nut-sedge | Alope-cures | Cucumber | Lambs-quarter | Crab Grass | Marigold | Tea-weed | Downy Brome | Flax | Buck-wheat | Mug-wort |
|---|---|---|---|---|---|---|---|---|---|---|---|---|---|
| 80 | 1-hydroxyantraquinone diphenylcarbamate | nt | 0 | nt | 4B 9R | nt | 4B 3C 7R | 4B 3R 1D | 1B | 0 | 10B | 1B | 9E 9R |
| 81 | 1-hydroxyanthraquinonyloxy N—methyl-N—phenyl carbamate | nt | 0 | nt | 7B 3R | nt | 3B | 3B 3R 10D | 2B 3C | 1B 2C | 10B | 1B | 2C |
| 82 | 1-hydroxy-4-methyl-anthraquinone | nt | 0 | nt | 6B 9R | nt | 10B | 7B 7R 10D | 10B | 0 | 10B | 10B | 0 |
| 83 | (1-anthraquinonyloxy)-acetic acid | nt | 0 | nt | 10B | nt | 10B | 10B | 10B | 9B | 10B | 2B | 1B |

The foregoing examples demonstrate the selective effectiveness of the compounds of the present invention on a post-emergence basis. The active state of growth of noxious weeds is substantially curtailed without appreciable detrimental effects on beneficial crops.

Although specific materials and conditions were set forth in the above examples for employing compounds containing the 1-anthraquinonyloxy moiety as herbicides for aquatic and terrestrial weeds, these are merely intended as illustrations of the present invention. Various other solvents, diluents, modes of application, concentrations and weeds such as those described hereinabove may be substituted in the examples with similar results.

Other modifications of the present invention will occur to those skilled in the art upon a reading of the present disclosure. These are intended to be included within the scope of this invention.

What is claimed is:

1. A method of inhibiting the growth of the weeds which comprises: applying to the situs to be treated an effective, herbicidal amount of an anthraquinone having the formula

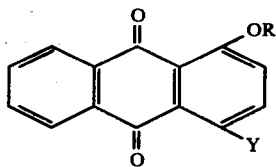

wherein Y is hydrogen or methyl, R is selected from the group consisting of hydrogen,

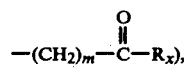

phenyl, and phenyl substituted with a radical of the group consisting of methyl, chloro, sulfamyl containing not more than 6 carbon atoms, sulfonyl chloride and methyl pyridinium chloride; and wherein m is 0 or 1 and $R_x$ is $-N(R_y)_2$ or a radical containing not more than 3 carbon atoms selected from the group consisting of alkyl, dichloroacrylate, chloroalkyl, chloroalkoxy, and alkoxy and wherein $R_y$ is selected from the group consisting of hydrogen, methyl, ethyl, phenyl and, when taken together with the nitrogen, forms a pyridinyl ring.

2. A method of inhibiting the growth of aquatic weeds, according to claim 1 by applying thereto an effective amount of 1-hydroxyanthraquinone.

3. A method as defined in claim 1 wherein the compound is applied in concentrations ranging from about 0.1 part to about 25 parts per million parts water.

4. A method as defined in claim 3 wherein the compound is applied in concentrations ranging from about 0.5 part to about 12 parts per million parts water.

5. A method as defined in claim 1 wherein the compound is 1-hydroxyanthraquinone.

6. A method as defined in claim 1 wherein the compound is applied in combination with an inert vehicle in concentrations ranging from about 0.1 pound to about 16 pounds per acre.

7. A method as defined in claim 1 wherein the weeds to be treated are aquatic weeds.

8. A method as defined in claim 1 wherein the compound is applied on a pre-emergence basis.

9. A method as defined in claim 1 wherein the compound is applied on a post-emergence basis.

* * * * *